United States Patent [19]

Imai et al.

[11] Patent Number: 4,486,547

[45] Date of Patent: Dec. 4, 1984

[54] INDIUM-CONTAINING DEHYDROGENATION CATALYST

[75] Inventors: Tamotsu Imai, Mount Prospect, Ill.; Chi-wen Hung, San Rafael, Calif.

[73] Assignee: UOP Inc., Des Plaines, Ill.

[21] Appl. No.: 500,472

[22] Filed: Jun. 2, 1983

Related U.S. Application Data

[63] Continuation-in-part of Ser. No. 318,520, Nov. 5, 1981, abandoned.

[51] Int. Cl.$^3$ .................. B01J 27/04; B01J 27/08; B01J 27/10; B01J 23/62
[52] U.S. Cl. ........................... 502/223; 502/226; 502/227; 502/328; 502/330; 502/334; 585/627; 585/629; 585/632
[58] Field of Search ............... 502/223, 226, 227, 328, 502/330, 334

[56] References Cited

U.S. PATENT DOCUMENTS

| | | | |
|---|---|---|---|
| 2,479,110 | 8/1949 | Haensel | 502/230 X |
| 2,814,599 | 11/1957 | Lefrancois et al. | 502/328 X |
| 2,914,464 | 11/1959 | Burton et al. | 208/138 |
| 3,745,112 | 7/1973 | Rausch | 502/227 X |
| 3,892,657 | 7/1975 | Wilhelm | 502/223 X |

FOREIGN PATENT DOCUMENTS 1499297 1/1978 United Kingdom .

*Primary Examiner*—Patrick Garvin
*Attorney, Agent, or Firm*—James R. Hoatson, Jr.; William H. Page, II; Kenneth J. Pedersen

[57] ABSTRACT

A new catalyst composition comprising a platinum group component, a tin component, an indium component, an alkali or alkaline earth component and a porous support material wherein the atomic ratio of indium to platinum group component is more than 1.0 is disclosed. The catalyst is particularly useful for dehydrogenating hydrocarbons. In one embodiment of the invention, detergent range normal paraffins ($C_{10}$–$C_{15}$ or higher) are dehydrogenated to the corresponding normal olefins in the presence of the subject catalyst and hydrogen.

11 Claims, 3 Drawing Figures

Time, Hours On Stream

INDIUM-CONTAINING DEHYDROGENATION CATALYST

CROSS-REFERENCE TO RELATED APPLICATION

This application is a continuation-in-part of prior copending application Ser. No. 318,520 filed Nov. 5, 1981 and now abandoned.

BACKGROUND OF THE INVENTION

1. Field of the Invention

This invention pertains to the conversion of hydrocarbons, especially the dehydrogenation of dehydrogenatable hydrocarbons, in the presence of a heterogeneous catalyst composite. Dehydrogenatable hydrocarbons contain at least two non-aromatic adjacent carbon atoms having one or two carbon-carbon bonds in common, each carbon atom of the pair having at least one hydrogen atom bonded to it. A heterogeneous catalyst is one which is in a phase different from the phase or phases of the reactants it catalyzes, for example, a solid catalyst which catalyzes liquid or gaseous reactants.

Dehydrogenating hydrocarbons is an important commercial process because of the great demand for dehydrogenated hydrocarbons for the manufacture of various chemical products such as detergents, high octane gasolines, pharmaceutical products, plastics, synthetic rubbers, and other products well known to those skilled in the art. One example of this process is dehydrogenating normal paraffin hydrocarbons having 2 to 20 or more carbon atoms per molecule to selectively produce corresponding normal mono-olefins. These normal mono-olefins are important to the detergent industry, for example, where they are utilized to alkylate an aromatic compound such as benzene with subsequent transformation of the product arylalkane into compounds for use in a wide variety of biodegradable household and industrial detergents.

2. Description of the Prior Art

Many components have been added to platinum group-containing compositions to obtain catalysts with improved performance. For example, U.S. Pat. Nos. 2,814,599 and 2,914,464 disclose adding primary activating agents selected from the group of gallium, indium, scandium, yttrium, lanthanum, thallium and actinium, and optional secondary activating agents selected from the group of mercury, zinc and cadmium, as well as optional promoting agents selected from the alcohols and ketones to obtain a platinum and/or palladium catalyst with improved reforming activity.

U.S. Pat. No. 3,745,112 discloses that tin is a good promoter for platinum group-containing reforming catalysts. This patent discloses also that a platinum-tin-alkali or alkaline earth composite is a particularly effective catalyst for dehydrogenating hydrocarbons. In the dehydrogenation catalyst composite of this patent the alkali or alkaline earth component is added and the amount of halogen is minimized in order to eliminate the isomerization and cracking reactions which occur on the acidic catalytic sites.

U.S. Pat. No. 3,892,657 discloses that indium is a good promoter for platinum group-containing reforming catalysts when the atomic ratio of indium to platinum is from about 0.1:1 to about 1:1. In column 4, lines 10–12, this patent discloses that only when the atomic ratio of indium to platinum is about 0.1 to 1.0 is the beneficial interaction of indium with platinum obtained. In column 25, lines 33–37, this patent discloses that when the atomic ratio is 1.35 or more, the beneficial effect of indium is not obtained. This patent discloses also that a Group IVA component selected from the group of germanium, tin, and lead can be added to the acidic form of the indiumcontaining catalysts for reforming applications. The acidic form of this catalyst, then, comprises a platinum group component, a Group IVA component, an indium component, a halogen component and a porous carrier material. For dehydrogenation applications this patent discloses a catalyst comprising a platinum group component, an indium component and an alkali or alkaline earth component with the porous carrier material. No catalyst comprising indium, platinum, tin, and an alkali or alkaline earth component is specifically disclosed in this patent.

British Pat. No. 1 499 297 discloses a dehydrogenation catalyst comprising platinum, at least one of the elements gallium, indium and thallium, and an alkali metal, especially lithium or potassium, with alumina as the carrier material. The disclosure of this patent is not limited to any specific atomic ratio of gallium or indium or thallium to platinum. No catalyst comprising tin is disclosed.

BRIEF SUMMARY OF THE INVENTION

Our invention relates to a new catalyst composition for dehydrogenating hydrocarbons. Also, our invention relates to a process for dehydrogenating hydrocarbons using the new catalyst as well as a method for manufacturing the catalyst. The catalyst comprises a platinum group component, a tin component, an indium component, an alkali or alkaline earth component and a porous support material wherein the atomic ratio of indium to platinum group component is about 1.6 or higher. The catalyst is particularly useful for dehydrogenating detergent range normal paraffins ($C_{10}$–$C_{15}$ or higher) to the corresponding normal olefins.

DETAILED DESCRIPTION OF THE INVENTION

Figure 1:
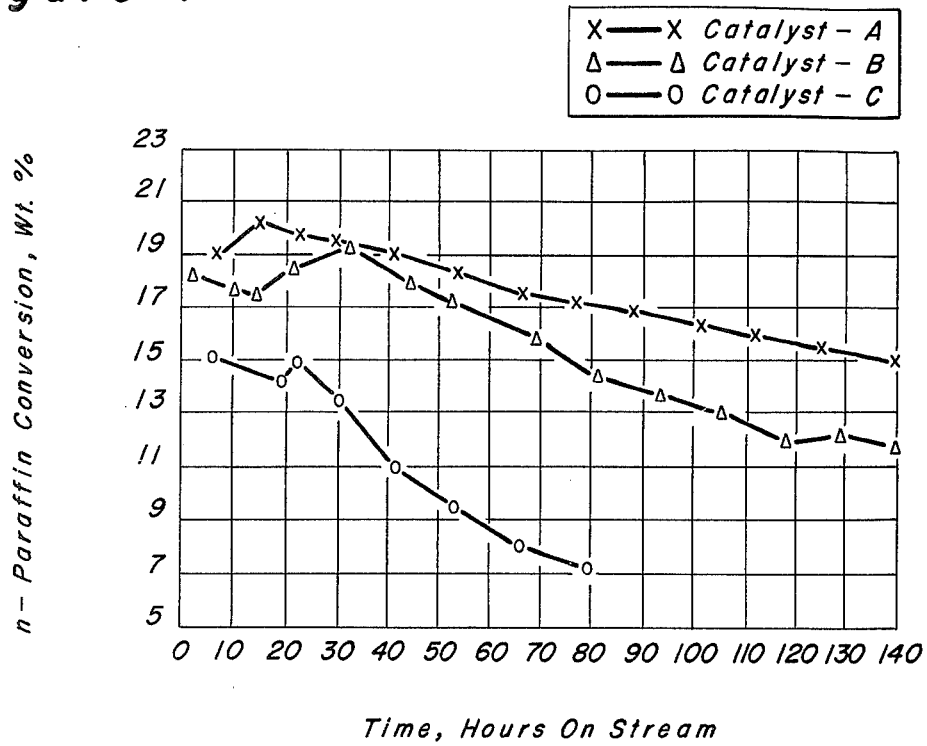
FIG. 1 illustrates normal paraffin conversion, in %, versus time, hours on stream, for the catalyst of this invention compared to representative catalysts of the prior art.

Heterogeneous catalysis practice, that is, catalyzing reactions of liquid or gaseous reactants with solid catalysts, is important to industry. For many years persons skilled in the art of hydrocarbon conversion have endeavored to discover and develop hydrocarbon conversion catalysts with improved performance characteristics. Many of these persons have been highly trained in one or more of a wide variety of disciplines including, for example, organic and inorganic chemistry, solid state and surface physics, ceramics, metallurgy and chemical engineering. Notwithstanding this high level of skill in the art, hydrocarbon conversion catalysis, like other types of heterogeneous catalysis, continues to be "a vast and confusing field replete with an enormous quantity of perhaps significant but empirical facts intermixed with perhaps useful theories. (C. N. Satterfield, *Heterogeneous Catalysis in Practice*, preface (1980).)

Consequently, significant contributions to the art of heterogeneous hydrocarbon conversion catalysis have generally resulted from empirical discoveries and developments rather than from theoretical extrapolations.

Our contribution to this field of art is that we have discovered a new catalyst composition comprising a platinum group component, a tin component, an indium component, an alkali or alkaline earth component and a porous support material wherein the atomic ratio of indium to platinum group component is about 1.6 or higher. Our composition is effective for catalyzing the dehydrogenation of dehydrogenatable hydrocarbons. The platinum group component is present in the final composite in an amount, calculated on an elemental basis, of about 0.01 to 5 wt. %; the tin component is present in an amount of about 0.01 to 5 wt. %; the indium component is present in an amount of about 0.01 to 15 wt. %; and the alkali or alkaline earth component is present in an amount of about 0.01 to 15 wt. %. For dehydrogenating detergent range normal paraffins ($C_{10}-C_{15}$ or higher) we have obtained best results when the catalyst comprises about 0.4 wt. % platinum, about 0.5 wt. % tin, about 0.6 wt. % lithium and about 0.3 wt. % indium when the indium component is impregnated on the alumina support. The atomic ratio of indium to platinum for this catalyst is about 1.3. We have obtained best results when the catalyst comprises about 0.4 wt. % platinum, about 0.5 wt. % tin, about 0.6 wt. % lithium and about 1.0 wt. % indium when the indium component is cogelled with the alumina support. The atomic ratio of indium to platinum for this catalyst is about 4.2. For commercial embodiments of this invention, we plan to maintain the indium to platinum atomic ratio at about 1.6 or higher.

Dehydrogenation conditions include a temperature of from about 400° to about 900° C., a pressure of from about 0.1 to 10 atmospheres and a liquid hourly space velocity (LHSV—defined as the volume amount, as a liquid at standard temperature, of hydrocarbon charged to the dehydrogenation zone per hour divided by the bulk volume of a fixed bed of the catalyst utilized) of from about 0.1 to 100 hr.$^{-1}$. The hydrocarbons to be dehydrogenated are dehydrogenatable hydrocarbons having from 2 to 20 or more carbon atoms including paraffins, alkylaromatics, naphthenes and olefins. The catalyst is particularly useful for dehydrogenating detergent range normal paraffins ($C_{10}-C_{15}$ or higher) to the corresponding normal olefins.

Our invention, then, is a new catalyst composition comprising a platinum group component, a tin component, an indium component, an alkali or alkaline earth component and a porous support material wherein the atomic ratio of indium to platinum group component is more than 1.0. Also, our invention is a method for converting hydrocarbons which comprises contacting the hydrocarbons, at hydrocarbon conversion conditions, with the catalyst of our invention. Also, our invention is a way of making the catalyst.

To be commercially successful a dehydrogenation catalyst must satisfy three essential requirements, namely high activity, high selectivity and good stability. Activity is a measure of the catalyst's ability to help convert reactants into products at a specified severity level where severity level means the reaction conditions used—that is, the temperature, pressure, contact time and presence of diluents such as hydrogen, if any. For dehydrogenation catalyst activity we measured the conversion, or disappearance of normal paraffins, in percent relative to the amount charged. Selectivity refers to the amount of desired product or products obtained relative to the amount of reactants charged or converted. For catalyst selectivity we measured the amount of normal olefins in the product, in weight percent, relative to the total weight of the product. Stability refers to the rate of change with time of the activity and selectivity parameters—the smaller rate implying the more stable catalysts. The slope of the activity versus time curve is the activity stability, for example.

Since dehydrogenation of hydrocarbons is an endothermic reaction and conversion levels are limited by chemical equilibrium, it is desirable in order to achieve high conversion to operate at high temperatures and low hydrogen partial pressures. Under such severe conditions it is difficult to maintain high activity and selectivity for long periods of time because at these conditions undesirable side reactions such as aromatization, cracking, coke formation, isomerization and polyolefin formation increase. Therefore, there is a considerable demand for a new hydrocarbon dehydrogenation catalyst with improved activity, selectivity and stability characteristics. The catalyst of our invention, that is, a catalyst comprising a platinum group component, a tin component, an indium component and an alkali or alkaline earth component with a porous support material wherein the atomic ratio of indium to platinum group component is more than 1.0, will answer to such a demand.

Regarding the platinum group component of our catalyst composite, it may be selected from the group of platinum or palladium or iridium or rhodium or osmium or ruthenium or mixtures thereof. Platinum, however, is the preferred platinum group component. We believe that substantially all of the platinum group component exists within the final catalytic composite in the elemental metallic state. Preferably the platinum group component is well dispersed throughout the catalytic composite. The platinum group component generally will comprise about 0.01 to about 5 wt. %, calculated on an elemental basis, of the final catalyst. Preferably the catalyst comprises about 0.4 wt. % platinum.

The platinum group component may be incorporated in the catalytic composite in any suitable manner such as by coprecipitation or cogelation, ion exchange or impregnation, or deposition from a vapor phase or from an atomic source either before, while or after the other catalytic components are incorporated. The preferred method of incorporating the platinum group component is to impregnate the support material with a solution or suspension of a decomposable compound of a platinum group metal. For example, platinum may be added to the support by commingling the latter with an aqueous solution of chloroplatinic acid. Another acid, for example, nitric acid or another optional component may be added to the impregnating solution to further assist in dispersing or fixing the platinum group component in the final catalyst composite.

The tin component of our catalyst composite is most likely present in an oxidation state above that of the elemental metal, that is, in the +2 or +4 oxidation state as a chemical compound such as the oxide, for example, or combined with the support material or with the other catalyst components. Preferably, the tin component is well dispersed throughout the catalytic composite. The tin component generally will comprise about 0.01 to about 5 wt. %, calculated on an elemental basis, of the final catalytic composite. Preferably the catalyst comprises about 0.5 wt. % tin.

The tin component may be incorporated into the catalytic composite in any suitable manner, including, for example, cogelation or coprecipitation with the support material, or ion exchange or impregnation of the support material with a suitable tin solution or suspension either before, while or after the other catalytic components are incorporated. A preferred method of incorporating the tin component is coprecipitating it during the preparation of the support material. For example, tin may be incorporated in an alumina support material by mixing a soluble tin compound such as stannous or stannic chloride with an alumina hydrosol, adding a gelling agent and dropping the mixture into an oil bath to form spheres containing alumina and tin.

The indium component of our catalyst composite, like the tin component, is preferably well dispersed throughout the composite in an oxidation state above that of the elemental metal. The indium component may be present as a chemical compound such as the oxide, for example, or combined with the support material or with the other catalyst components. The indium component generally will comprise about 0.01 to about 15 wt. %, calculated on an elemental basis, of the final catalyst. Preferably the catalyst comprises about 0.3 wt. % indium when the indium component is impregnated on the support material, and about 1 wt. % indium when the indium component is cogelled with the support material. About three times as much indium is required to obtain comparable results when the indium component is cogelled with the support material than when it is impregnated on the support material.

The indium component may be incorporated into the catalytic composite in any suitable manner, including, for example, cogelation or coprecipitation with the carrier material, or ion exchange or impregnation of the carrier material with a suitable indium solution or suspension either before, while or after the other catalytic components are incorporated. We have obtained good results both when the indium component has been incorporated by coprecipitating it during the preparation of an alumina carrier material from a mixture of an alumina hydrosol, a gelling agent and a soluble indium compound such as indium chloride or indium nitrate, for example, and by impregnating it on the prepared alumina material from a solution of indium chloride or indium nitrate, for example.

For our catalyst, the atomic ratio of indium to platinum group component is more than 1.0. Preferably it is more than 1.35. More preferably it is more than 1.5. In pilot plant tests dehydrogenation catalysts with atomic ratios more than 1.0 exhibited higher stability, represented by less decrease in activity per hour on stream, than similar catalysts with atomic ratios less than 1.0.

The alkali or alkaline earth component of the catalyst of our invention is selected from the group of cesium, rubidium, potassium, sodium and lithium or from the group of barium, strontium, calcium and magnesium or mixtures of metals from either or both of these groups. Lithium, however, is the preferred alkali or alkaline earth component. We believe the alkali or alkaline earth component exists in the catalytic composite of my invention in an oxidation state above that of the elemental metal. The alkali or alkaline earth component may be present as a compound such as the oxide, for example, or combined with the carrier material or with the other components. Preferably the alkali or alkaline earth component is well dispersed throughout the catalytic composite. The alkali or alkaline earth component generally will comprise about 0.01 to 15 wt. %, calculated on an elemental basis, of the final catalytic composite. Preferably the catalyst comprises about 0.6 wt. % lithium.

The alkali or alkaline earth component may be incorporated in the catalytic composite in any suitable manner, for example, by cogelation or coprecipitation, by ion exchange or impregnation, or by like procedures either before, while or after the other catalytic components are incorporated. We have obtained best results when lithium has been added to the carrier material from an impregnating solution of lithium nitrate.

The porous support material of the catalytic composite of our invention is preferably a porous, absorptive support with high surface area of from about 25 to about 500 m$^2$/g. The porous support material should be relatively refractory to the conditions utilized in the hydrocarbon dehydrogenation process. It is intended to include within the scope of our invention the use of carrier materials which have traditionally been utilized in hydrocarbon conversion catalysts such as, for example; (1) activated carbon, coke, or charcoal; (2) silica or silica gel, silicon carbide, clays, and silicates including those synthetically prepared and naturally occurring, which may or may not be acid treated, for example, attapulgus clay, china clay, diatomaceous earth, fuller's earth, kaolin, kieselguhr, etc.; (3) ceramics, porcelain, crushed firebrick, bauxite; (4) refractory inorganic oxides such as alumina, titanium dioxide, zirconium dioxide, chromium oxide, beryllium oxide, vanadium oxide, cesium oxide, hafnium oxide, zinc oxide, magnesia, boria, thoria, silica-alumina, silica-magnesia, chromia-alumina, alumina-boria, silica-zirconia, etc.; (5) crystalline zeolitic silicates such as naturally occurring or synthetically prepared mordenite, faujasite, silicalite or other zeolites, either in the hydrogen form or in a form which has been exchanged with metal cations; (6) spinels such as $MgAl_2O_4$, $FeAl_2O_4$, $ZnAl_2O_4$, $CaAl_2O_4$, and other like compounds having the formula $MO-Al_2O_3$ where M is a metal having a valence of 2; and (7) combinations of materials from one or more of these groups. The preferred support material for our catalyst is alumina, especially gamma- or eta-alumina.

The preferred alumina carrier material may be prepared in any suitable manner from synthetically prepared or naturally occurring raw materials. The carrier may be formed in any desired shape such as spheres, pills, cakes, extrudates, powders, granules, etc., and it may be utilized in any particle size. A preferred form of alumina is the sphere. A preferred particle size is about 1/16 inch in diameter, though particles as small as about 1/32 inch, and smaller, may also be utilized.

To make alumina spheres an alumina powder is converted into an alumina sol by reacting the powder with a suitable peptizing acid and water, and then dropping a mixture of the resulting sol and a gelling agent into an oil bath to form spherical particles of an alumina gel which are easily converted into the gamma-alumina carrier material by known methods including aging, drying and calcining. To make alumina cylinders, an alumina powder is mixed with water and a suitable peptizing agent such as nitric acid, for example, until an extrudable dough is formed. The dough is then extruded through a suitable sized dye to form extrudate particles. Other shapes of the alumina carrier material may also be prepared by conventional methods. After the alumina particles are shaped generally they are dried and calcined. The alumina support carrier may be subjected to intermediate treatments during its preparation, including washing with water or contacting with ammonium hydroxide, for example, which treatments are generally well known in the art. Other components may be added to the preferred alumina carrier material during its preparation. For example, the tin component and/or the indium component can be cogelled or coprecipitated with the alumina hydrosol or they may be added to the extrudable alumina dough, etc.

Optionally the catalytic composite of our invention may contain a halogen component. The halogen component may be either fluorine, chlorine, bromine or mixtures thereof. Chlorine is the preferred halogen component. The halogen component is generally present, we believe, in a combined state with the porous carrier material. Preferably the halogen component is well dispersed throughout the catalytic composite. The halogen component, if any, generally will comprise about 0.01 to about 15 wt. %, calculated on an elemental basis, of the final catalytic composite.

The halogen component may be added to the carrier material in any suitable manner, either during the preparation of the support or before, while or after the other catalytic components are incorporated. For example, the alumina hydrosol utilized to form the preferred alumina carrier material may contain halogen and thus contribute at least some portion of the halogen content in the final catalyst composite. Also, the halogen component or a portion thereof may be added to the catalyst composite during the impregnation of the carrier material with the other catalyst components, for example, by using chloroplatinic acid to impregnate the platinum component. Also, a halogen component may be added to the catalyst composite by adding the halogen or a compound containing the halogen such as propylene dichloride, for example, to the hydrocarbon feed stream or to the recycle gas during operation of the dehydrogenation process. Or, the halogen component may also be incorporated by contacting the catalyst with the halogen or a compound, solution or suspension containing the halogen in a subsequent catalyst regeneration step. In the regeneration step carbon deposited on the catalyst as coke during use of the catalyst during the dehydrogenation process is burned off the catalyst and the platinum group component which has become agglomerated on the catalyst is redistributed to provide a regenerated catalyst with performance characteristics much like the fresh catalyst.

Optionally the catalyst composite of our invention can also contain a sulfur component. Generally the sulfur component will comprise about 0.01 to about 1.0 wt. %, calculated on an elemental basis, of the final catalytic composite. The sulfur component may be incorporated into the catalytic composite in any suitable manner. Preferably sulfur or a compound containing sulfur such as hydrogen sulfide or a lower molecular weight mercaptan, for example, is contacted with the catalyst composite in the presence of hydrogen at a hydrogen to sulfur ratio of about 10 and a temperature of from about 10° to about 540° C., preferably under water-free conditions, to incorporate the sulfur component.

Preferably the catalyst composite of our invention is nonacidic. "Nonacidic" in this context means that the catalyst has very little isomerization activity, that is, the catalyst converts less than 10 mole % of 1-butene to isobutylene when tested at dehydrogenation conditions and, preferably, converts less than 1 mole %. The acidity of the catalyst can be minimized to make the catalyst nonacidic by increasing the amount of the alkali or alkaline earth component and/or by minimizing the amount of the halogen component. The amount of halogen component can be minimized by subjecting the catalyst composite to a treatment with high temperature steam or a mixture of steam and a diluent gas such as air or hydrogen or nitrogen.

After the catalyst components have been combined with the porous carrier material, the resulting catalyst composite will generally be dried at a temperature of from about 100° to about 320° C. for a period typically of about 1 to about 24 hours or more and thereafter calcined at a temperature of about 320° to about 600° C. for a period of about 0.5 to about 10 or more hours. The acidity of the catalyst composite is preferably adjusted during or after the calcination step by treating the calcined composite with high temperature steam or with a mixture of steam and a diluent gas in the manner described earlier. Finally the calcined and possibly acid adjusted catalyst composite is typically subjected to a reduction step before use in the dehydrogenation process. Preferably, a substantially pure and dry hydrogen stream is used as the reducing agent in this step. This reduction step is effected at a temperature of about 230° to about 650° C. for a period of about 0.5 to about 10 or more hours, the temperature and time being selected to be long and hot enough to reduce substantially all of the platinum group component to the elemental metallic state.

According to the method of the present invention the dehydrogenatable hydrocarbons are contacted with the catalytic composite of our invention in a dehydrogenation zone maintained at dehydrogenation conditions. This contacting may be accomplished in a fixed catalyst bed system, a moving catalyst bed system, a fluidized catalyst bed system, etc., or in a batch type operation. A fixed bed system is preferred. In this fixed bed system the hydrocarbon feed stream is preheated to the desired reaction temperature and then passed into the dehydrogenation zone containing a fixed bed of the catalyst. The dehydrogenation zone may itself comprise one or more separate reaction zones with heating means therebetween to insure that the desired reaction temperature can be maintained at the entrance to each reaction zone. The hydrocarbon, preferably in the vapor phase, although it may be in a mixed vapor-liquid phase or in the liquid phase, may be contacted with the catalyst bed in either upward, downward or radial flow fashion. Radial flow of the hydrocarbon through the catalyst bed is preferred for commercial scale reactors.

Conditions in the dehydrogenation zone include a temperature of from about 400° to about 900° C., a pressure of from about 0.1 to 10 atmospheres and a liquid hourly space velocity (LHSV) of from about 0.1 to 100 hr.$^{-1}$. Generally, for normal paraffins the lower the molecular weight of the hydrocarbon the higher the temperature required for comparable conversion. The pressure in the dehydrogenation zone is maintained as low as practicable, consistent with equipment limitations, to maximize the equilibrium advantages.

The effluent stream from the dehydrogenation zone generally will contain unconverted dehydrogenatable hydrocarbons, hydrogen and the products of dehydrogenation reactions. This effluent stream is typically cooled and passed to a hydrogen separation zone to separate a hydrogen-rich vapor phase from a hydrocarbon-rich liquid phase. Generally, the hydrocarbon-rich liquid phase is further separated by means of either a suitable selective adsorbent, a selective solvent, a selective reaction or reactions or by means of a suitable fractionation scheme. Unconverted dehydrogenatable hydrocarbons are recovered and may be recycled to the dehydrogenation zone. Products of the dehydrogenation reactions are recovered as final products or as intermediate products in the preparation of other compounds.

The dehydrogenatable hydrocarbons may be admixed with a diluent material prior, while or after being passed to the dehydrogenation zone. The diluent material may be hydrogen, steam, methane, ethane, carbon dioxide and the like. Hydrogen is the preferred diluent. Ordinarily, when hydrogen is utilized as the diluent it is utilized in amounts sufficient to insure a hydrogen to hydrocarbon mole ratio of about 1:1 to about 40:1, with best results being obtained when the mole ratio range is about 1.5:1 to about 10:1. The diluent hydrogen stream passed to the dehydrogenation zone will typically be recycled hydrogen separated from the effluent from the dehydrogenation zone in the hydrogen separation zone.

Water or a material which decomposes at dehydrogenation conditions to form water such as an alcohol, aldehyde, ether or ketone, for example, may be added to the dehydrogenation zone, either continuously or intermittently, in an amount to provide, calculated on the basis of equivalent water, about 1 to about 20,000 wt. ppm of the hydrocarbon feed stream. About 1 to about 10,000 wt. ppm of water addition gives best results when dehydrogenating detergent range normal paraffins.

The following worked Examples are introduced to describe further the catalyst of our invention and to teach one skilled in the art how to make it and how to use it in the dehydrogenation process of our invention. These Examples represent specific embodiments of our invention and are intended to be illustrative only and not restrictive.

EXAMPLE I

A catalyst composite, hereinafter catalyst "A", was prepared to represent the catalyst of our invention. The catalyst comprised about 0.4 wt. % platinum, about 0.5 wt. % tin, about 0.3 wt. % indium and about 0.6 wt. % lithium on a carrier of gamma-alumina. The atomic ratio of indium to platinum for this catalyst was 1.27. The catalyst was prepared by dissolving substantially pure aluminum pellets in a hydrochloric acid solution, thereafter dissolving in this sol an amount of stannic chloride calculated to provide a final composite containing about 0.5 wt. % tin, and then stirring the sol vigorously to distribute the tin component evenly throughout it. Hexamethylenetetramine was then added to the sol and the resulting mixture was dropped into an oil bath in a manner to form spherical particles having an average particle diameter of about 1/16 inch. Thereafter the spheres were aged and washed with an ammoniacal solution, then dried and calcined to form a spherical gamma-alumina carrier material containing about 0.5 wt. % tin in the form of tin oxide. More details about this method of preparing the preferred alumina carrier material are disclosed in U.S. Pat. No. 2,620,314.

Then, 90 g (300 cc) of the tin-containing alumina carrier was contacted with 300 cc of a solution of 0.6 g of indium nitrate dissolved in 3.2 cc of 70.8% nitric acid, 5.4 g of lithium nitrate and water in a rotary drier at room temperature under nitrogen for 15 minutes. Then steam was passed to the jacket of the drier and the water was driven off, leaving the indium and lithium components incorporated with the tin-containing alumina carrier. This composite was then calcined in a quartz tube furnace at 550° C. with 300 hr.$^{-1}$ gas hourly space velocity (GHSV—defined as the volume amount, as gas at standard temperature and pressure, of treating gas charged to the calcination zone per hour divided by the bulk volume of the catalyst being calcined) of a 50/50 air/80° C. steam mixture for 6 hours. Then, the tin, indium, lithium and alumina composite was contacted with 300 cc of a solution of 7.5 cc of 0.452 g/cc chloroplatinic acid solution and 3.2 cc of 70.8% nitric acid and water in a rotary drier at room temperature under nitrogen for 15 minutes. Then, this mixture was also steamed to dryness, and calcined at 540° C. with 300 hr.$^{-1}$ gas hourly space velocity (GHSV) of a 50/50 air/80° C. steam mixture for 2 hours. This catalyst "A" and, alternatively, catalyst "D" in Example 2, represent preferred embodiments of my catalytic composite.

A different prior art catalyst, hereinafter catalyst "B", was prepared to represent the dehydrogenation catalyst disclosed in U.S. Pat. No. 3,745,112. This catalyst comprised 0.4 wt. % platinum, 0.5 wt. % tin and 0.6 wt. % lithium. It was prepared in the same manner as catalyst "A" above, except the indium component, required for the catalyst of our invention, was not added to catalyst "B".

Another different prior art catalyst, hereinafter catalyst "C", was prepared to represent one of the dehydrogenation catalysts disclosed in British Pat. No. 1 499 297. This catalyst comprised 0.4 wt. % platinum, 0.3 wt. % indium and 0.54 wt. % lithium. It was prepared in the same manner as catalyst "A" above, except that the tin component required for the catalyst of our invention, was not added to catalyst "C".

All of these catalysts contained a small amount of sulfur component which was incorporated in a sulfiding step at 485° C. and 1 atmosphere pressure from a 1% mixture of hydrogen sulfide in hydrogen gas at 3,100 hr.$^{-1}$ gas hourly space velocity (GHSV) for 5 hours. After the sulfiding step these catalysts contained approximately 0.1 wt. % sulfur, calculated on an elemental basis.

All of these catalysts were reduced in a reduction step prior to being tested. Reduction conditions were; 485° C. and 1 atmosphere presssure in hydrogen gas at 7,900 hr.$^{-1}$ GHSV for 1 hour.

These catalysts were all tested for dehydrogenation activity, selectivity and stability in a laboratory scale dehydrogenation plant comprising a reactor, a hydrogen separation zone, and heaters, coolers, pumps, compressors, and the like conventional equipment for handling hydrocarbons. In this plant, the feed stream containing the dehydrogenatable hydrocarbon is combined with a hydrogen gas stream and the resulting mixture is heated to the desired conversion temperature which is measured at the inlet to the dehydrogenation reactor. The heated mixture then contacts the fixed bed of catalyst in downflow fashion. The pressures reported herein are measured at the outlet from the reactor. An effluent stream is withdrawn from the reactor, cooled, and passed into the hydrogen separation zone to separate a hydrogen-rich gas phase from the hydrocarbon-rich liquid phase. The hydrocarbon-rich liquid phase is withdrawn from the hydrogen separation zone and analyzed to measure the amount of conversion, or activity, and the relative amount of desired dehydrogenated hydrocarbons, or selectivity, for the catalyst composite being tested. Conversion numbers reported herein are calculated on the basis of disappearance of normal paraffins, expressed in wt. %, of the feed stream. Similarly, selectivity numbers reported are calculated on the basis of desired normal olefins produced, expressed in wt. %, of the liquid product recovered.

The same normal paraffin feed stream was used in all the tests. It comprised in wt. %;
n-Decane: 0.3
n-Undecane: 28.5
n-Dodecane: 35.8
n-Tridecane: 26.7
n-Tetradecane: 8.0
Total Linear Paraffins: 99.3
Total Non-Linear Paraffins: 0.7

Reaction conditions were generally the same for all tests. They were; 485° C., 2.4 atmospheres, 6 hydrogen to hydrocarbon mole ratio, 20 hr.$^{-1}$ liquid hourly space velocity (LHSV) for the tests of catalysts "B" and "C", and 17 hr.$^{-1}$ LHSV for the test of catalyst "A". In our opinion, the slightly lower LHSV for the test of catalyst "A" did not substantially effect the comparison of catalyst "A" with catalysts "B" and "C" as reported. Results from the tests are presented in FIGS. 1 and 2.

Figure 2:
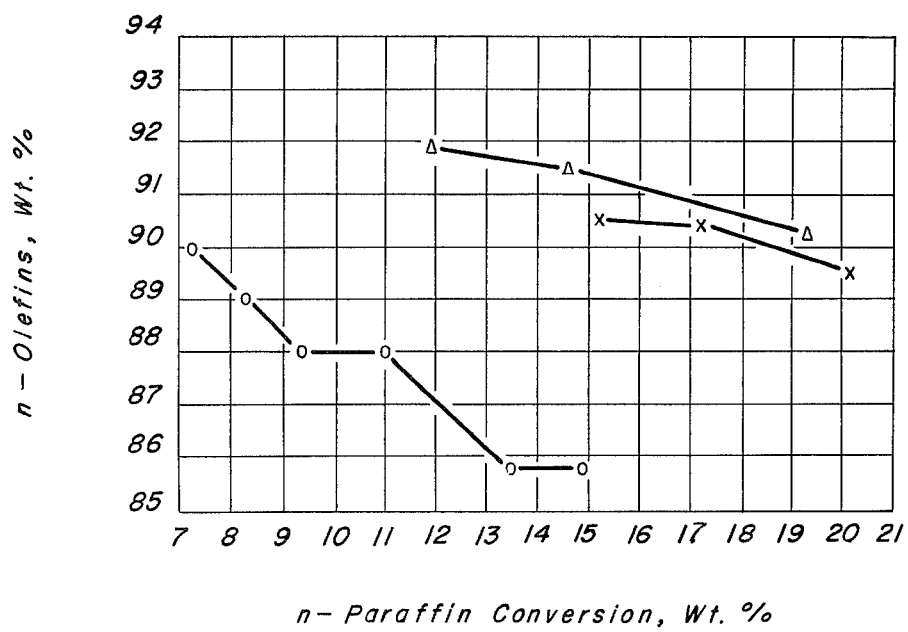
FIG. 2 illustrates selectivity to total normal olefins, in wt. %, versus conversion, for the same catalysts. These Figures illustrate that more conversion and more conversion stability and similar selectivity is obtained with the catalyst of this invention compared with the prior art catalysts.

FIG. 1 clearly shows that the catalyst of our invention, catalyst "A" comprising platinum, tin, indium and lithium, possesses superior activity and activity stability compared to the prior art catalyst "B" comprising platinum, tin and lithium, but without indium, and compared to the prior art catalyst "C" comprising platinum, indium and lithium, but without tin. FIG. 2 shows that the selectivity and selectivity stability of our catalyst "A" is comparable to the best of these prior art catalysts.

EXAMPLE II

A catalyst composite, hereinafter catalyst "D", was prepared to represent the catalyst of our invention. The catalyst comprised about 0.4 wt. % platinum, about 0.5 wt. % tin, about 1.3 wt. % indium and about 0.6 wt. % lithium on a carrier of gamma-alumina. The atomic ratio of indium to platinum for this catalyst was 5.52. The alumina carrier material for this catalyst was prepared in the same manner as for catalyst "A" in Example I above, except the indium component was incorporated by dissolving an amount of indium nitrate, calculated to provide a final composite containing about 1.0 wt. % indium, in the alumina sol. Then 24 g (100 cc) of the tin and indium-containing alumina carrier was contacted with 100 cc of a solution of 0.10 g of platinum from chloroplatinic acid, 0.15 g of lithium from lithium nitrate, 0.75 g of nitric acid and water in a rotary drier at room temperature under nitrogen for 15 minutes. Then the mixture was dried, leaving the platinum and lithium components incorporated with the tin and indium-containing alumina carrier. This composite was then calcined in air for 1 hour at 540° C., with the warm-up from room temperature and the cool-down to room temperature in nitrogen.

A different catalyst, hereinafter catalyst "E", comprising 0.4 wt. % platinum, 0.3 wt. % germanium, 1.1 wt. % indium and 0.6 wt. % lithium was prepared in the same manner as catalyst "D" above, except germanium, in the form of germanium chloride, was added to the alumina sol instead of tin.

Another different catalyst, hereinafter catalyst "F", comprising 0.4 wt. % platinum, 0.8 wt. % lead, 1.0 wt. % indium and 0.6 wt. % lithium was prepared in the same manner as catalyst "D" above, except lead, in the form of lead aftate, was added to the alumina sol instead of tin.

These catalysts were not subjected to the sulfiding step utilized in the tests of the catalysts "A", "B" and "C" in Example I. These catalysts were reduced in the same manner as the catalysts in Example I, however.

The same feed stream and reaction conditions utilized in Example I were also utilized to test these catalysts, except the LHSV for all of these catalysts was 28 hr.$^{-1}$. In our opinion, the slightly higher wt. % of indium in catalyst "D" did not substantially effect the comparison of catalyst "D" with catalysts "E" and "F" as reported. Results from the tests are presented in FIG. 3.

Figure 3:
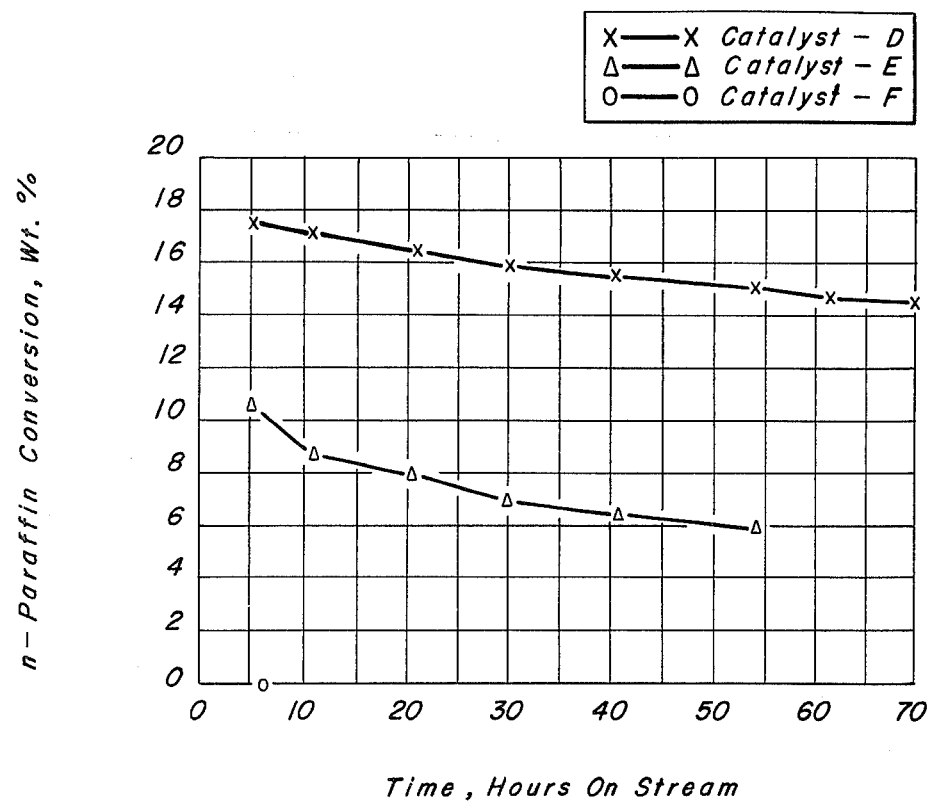
FIG. 3 illustrates normal paraffin conversion, in %, versus time, hours on stream, for the catalyst of this invention comprising tin compared with other similar catalysts comprising, instead of tin, germanium and lead. This Figure illustrates the superior performance of the catalyst of this invention for dehydrogenating normal paraffins compared with similar catalysts comprising other Group IVA metal components.

FIG. 3 clearly shows that the catalyst of our invention, catalyst "D" comprising platinum, tin, indium and lithium, possesses superior activity and activity stability compared to similar catalysts "E" and "F" comprising, instead of tin, other Group IVA metals, namely germanium and lead, respectively.

EXAMPLE III

We studied the effect of the indium to platinum group component atomic ratio on the activity stability of dehydrogenation catalysts comprising a platinum group component, a tin component, an indium component, an alkali or alkaline earth component and a porous support material. Five catalysts were prepared generally in the same manner as for catalysts in the preceding EXAMPLES. Catalyst "G" comprised 0.364 wt. % platinum, 0.5 wt. % tin and 0.6 wt. % lithium. This catalyst contained no indium component. Catalyst "H" comprised 0.366 wt. % platinum, 0.5 wt. % tin, 0.11 wt. % indium and 0.6 wt. % lithium. Catalyst "I" comprised 0.375 wt. % platinum, 0.5 wt. % tin, 0.26 wt. % indium and 0.6 wt. % lithium. Catalyst "J" comprised 0.386 wt. % platinum, 0.5 wt. % tin, 0.34 wt. % indium and 0.6 wt. % lithium. Catalyst "K" comprised 0.415 wt. % platinum, 0.5 wt. % tin, 0.39 wt. % indium and 0.6 wt. % lithium. All these catalysts were sulfided to a level of about 0.1 wt. % sulfur.

These catalysts were tested for dehydrogenation of normal $C_{11}$-$C_{14}$ paraffins in a laboratory plant like the one described in EXAMPLE I. The feed stream comprised in wt. %:
n-Decane: 0.3
n-Undecane: 28.6
n-Dodecane: 35.7
n-Tridecane: 26.6
n-Tetradecane: 8.1

Reaction conditions, which were the same for all tests, were: 485° C., 2.4 atmospheres, 6 hydrogen to hydrocarbon mole ratio and 20 hr.$^{-1}$ LHSV. 2,000 wt. ppm water was added to the dehydrogenation zone. In our opinion, the slightly higher wt. % platinum for catalysts "H", "I", "J" and "K" did not substantially effect their comparison with catalyst "G" as reported. Results from the tests are summarized in TABLE I.

TABLE I

| Catalyst | In/Pt Atomic Ratio | Relative Activity Stability |
|---|---|---|
| G | 0 | 1.0 |
| H | 0.51 | 1.14 |
| I | 1.18 | 1.39 |
| J | 1.50 | 1.61 |
| K | 1.60 | 4.0 |

From TABLE I it is apparent that dehydrogenation catalysts with added indium component exhibited higher activity stability than a reference catalyst without indium. Furthermore, the beneficial effect of indium was realized for catalysts with indium to platinum ratios more than 1.0. Best stability was obtained for the catalysts with the highest indium to platinum ratios.

We claim as our invention:

1. A catalyst composition comprising a platinum group component, a tin component, an indium component, an alkali or alkaline earth component and a porous support material wherein the atomic. ratio of indium to platinum group component is about 1.6, or higher.

2. The catalyst of claim 1 wherein the platinum group component comprises platinum.

3. The catalyst of claim 1 wherein the alkali or alkaline earth component comprises lithium.

4. The catalyst of claim 1 wherein the porous support material is alumina.

5. The catalyst of claim 1 which comprises, calculated on an elemental basis, about 0.01 to 5 wt. % platinum group component, about 0.01 to 5 wt. % tin, about 0.01 to 15 wt. % indium and about 0.01 to 15 wt. % alkali or alkaline earth component.

6. The catalyst of claim 1 which comprises about 0.01 to about 15 wt. % halogen component.

7. The catalyst of claim 1 which comprises about 0.01 to about 1.0 wt. % sulfur component.

8. A catalyst composition comprising a platinum group component, a tin component, an indium component, an alkali or alkaline earth component and a porous support material wherein the atomic ratio of indium to platinum group component is about 1.6, or higher, said catalyst being nonacidic.

9. A method for making a catalyst which comprises incorporating a platinum group component, a tin component, an indium component and an alkali or alkaline earth component with a porous support material so that the atomic ratio of indium to platinum group component is about 1.6, or higher.

10. The method of claim 9 wherein the indium component is impregnated on the support material.

11. The method of claim 9 wherein the indium component is cogelled with the support material.

* * * * *